United States Patent [19]
Ingram

[11] Patent Number: 6,130,076
[45] Date of Patent: *Oct. 10, 2000

[54] ETHANOL PRODUCTION USING A SOY HYDROLYSATE-BASED MEDIUM OR A YEAST AUTOLYSATE-BASED MEDIUM

[75] Inventor: Lonnie O. Ingram, Gainesville, Fla.

[73] Assignee: University of Florida Research Foundation, Inc., Gainesville, Fla.

[*] Notice: This patent issued on a continued prosecution application filed under 37 CFR 1.53(d), and is subject to the twenty year patent term provisions of 35 U.S.C. 154(a)(2).

[21] Appl. No.: 08/879,005

[22] Filed: Jun. 19, 1997

[51] Int. Cl.$^7$ ...................................................... C12P 7/06
[52] U.S. Cl. ............................................................. 435/161
[58] Field of Search ............................................. 435/161

[56] References Cited

PUBLICATIONS

York, S.W. and Ingram, L.O., "Soy–based medium for ethanol production by *Escherichia coli* KO11," *Journal of Industrial Microbiology*, 16:374–376 (1996).

York, S.W. and Ingram, L.O., "Ethanol Production by Recombinant *Escherichia coli* KO11 Using Crude Yeast Autolysate as a Nutrient Supplement," *Biotechnology Letters*, 18(6):683–688 (Jun. 1996).

Amartey, S., and Jeffries, T.W., "Comparison of corn steep liquor with other nutrients in the fermentation of D–xylose by *Pichia stipitis* CBS 6054," *Biotechnol. Lett.*, 16:211–214 (1994).

Asghari, A., Bothast, R.J., Doran, J.B., Ingram, L.O., "Ethanol production from hemicellulose hydrolysates of agricultural residues using genetically engineered *Escherichia coli* strain KO11," *J. Ind. Microbiol.*, 16:42–47 (1996).

Atkinson, B., Mavituna F., *Biochemical Engineering and Biotechnology Handbook*, $2^{nd}$ edn., Stockton Press, New York, NY (1991).

"Free amino nitrogen" In *Analytica–EBC*, $4^{th}$ edn., European Brewery Convention, Zurich, Switzerland, pp. E141–E142, 1987.

Guimaraes, W.V., Dudey G.L., and Ingram, L.O., "Fermentation of sweet whey by ethanologenic *Escherichia coli*," *Biotechnol. Bioeng.*, 40:41–45 (1992).

Jones, A.M., and Ingledew, W.M., "Fermentation of very high gravity wheat mash prepared using fresh yeast autolysate," *Biores. Technol.*, 50:97–101 (1994a).

Jones, A.M., and Ingledew, W.M., "Fuel alcohol production: appraisal of nitrogenous yeast foods for very high gravity wheat mash fermentation," *Process Biochem.*, 29:483–488 (1994b).

Kollar, R., Sturdik, E., and Sajbidor, J., "Complete fractionation of *Saccharomyces cervisiae* biomass," *Food Biotechnol.*, 6:225–237 (1992).

Shah, M.M. and Cheryan, M., "Acetate production by *Clostridium thermoaceticum* in corn steep liquor media," *J. Indust. Microbiol.*, 15:424–428 (1995).

Thomas, K.C., and Ingledew, W.M., "Fuel alcohol production: effects of free amino nitrogen on fermentation of very–high–gravity wheat–mashes," *Appl. Environ. Microbiol.* 56:2046–2050 (1990).

Zabriskie, D.W., Armiger, W.B., Phillips, D.H., and Albano, P.A., *Traders' Guide to Fermentation Media Formulation*, Traders Protein, Memphis, TN (1988).

Lawford, H.G., and Rousseau J.D., Ethanol production by recombinant *Escherichia coli* carrying genes from *Zymomonas mobilis*. *Appl. Biochem. Biotechnol.*, 28/29:221–236 (1991).

*Primary Examiner*—Herbert J. Lilling
*Attorney, Agent, or Firm*—Lahive & Cockfield, LLP; Elizabeth A. Hanley, Esq.; Peter C. Lauro, Esq.

[57] ABSTRACT

This invention presents a method for the production of ethanol that utilizes a soy hydrolysate-based nutrient medium or a yeast autolysate-based medium nutrient medium in conjunction with ethanologenic bacteria and a fermentable sugar for the cost-effective production of ethanol from lignocellulosic biomass. The invention offers several advantages over presently available media for use in ethanol production, including consistent quality, lack of toxins and wide availability.

15 Claims, 2 Drawing Sheets

ETHANOL PRODUCTION USING A SOY HYDROLYSATE-BASED MEDIUM OR A YEAST AUTOLYSATE-BASED MEDIUM

GOVERNMENT FUNDING

This invention was made, in part, with support by grants from the United States Department of Agriculture National Research Initiative (58-3620-2-112 and 95-37308-1843), the United States Department of Energy Basic Energy Sciences (FG05-86ER3574) and the Florida Agricultural Experiment Station (Publication Nos. R-05029 and R-05050).

BACKGROUND OF THE INVENTION

The development of cost-effective methods for the conversion of lignocellulose to ethanol offers many potential opportunities to solve environmental waste problems and to replace petroleum-based automotive fuels (Hohmann, et al., 1993; Sheehan, 1994). However, it is difficult to produce high ethanol concentrations from most lignocellulosic biomass.

Recently, recombinant microorganisms have been developed that produce higher ethanol concentrations from lignocellulose relative to other microorganisms. For example, *E. coli* KO11 is a recombinant derivative of *E. coli* B in which the *Zymomonas mobilis* genes encoding pyruvate decarboxylase (pdc) and alcohol dehydrogenase (adhB) have been integrated into the host chromosome (Ohta et al., 1991 and U.S. Pat. Nos. 5,000,000; 5,028,539; 5,424,202; and 5,482, 846). Genetically engineered bacteria, such as *Escherichia coli* KO11, have been shown to be effective biocatalysts for the fermentation of hemicellulose hydrolysates (Beall et al., 1992) and mixed waste office paper (Brooks and Ingram, 1995), achieving ethanol levels of 40–50 $gL^{-1}$ within 48 to 72 h (Katzen and Fowler, 1994). However, to achieve these levels of ethanol production, fermenting and processing of up to 20 L of broth per liter of ethanol is required. Thus, there is a need for an inexpensive nutrient media to make ethanol production from lignocellulosic biomass economically feasible.

As with yeast (Jones et al., 1994; Thomas et al., 1990), the rate of fermentation and ethanol yield with ethanologenic bacteria are higher when complex nutrients are added (Lawford et al., 1991). Amino nitrogen has been identified as being of particular importance (Guimaraes et al., 1992; Jones et al., 1994a; Thomas et al., 1990). Additionally, organic nitrogen, amino acids, and commercial proteases are marketed as supplements for the yeast-based ethanol industries (Jones et al., 1994b). However, commercial, purified protein hydrolysates are too costly ($3.50–$18.00 $kg^{-1}$ in bulk) for ethanol production.

Corn steep liquor is widely used as an inexpensive microbial nutrient supplement (Atkinson and Mavituna, 1991) and supports excellent ethanol production by the pentose-fermenting yeast Pichia stipitis (Amartey and Jeffries, 1994) and *E. coli* KO11 (Asghari et al., 1996). Corn steep liquor, however, has a number of problems, including a lack of availability in some areas and variations in quality (Shah and Cheryan, 1995). Most importantly, corn steep liquor contains toxins which require removal prior to use. The removal of toxins adds additional steps and expense in the production of ethanol. Additionally, the variations in quality mean that additional testing must be conducted each time a new batch of corn steep liquor is used so that the corn steep liquor can be optimized in conjunction with the other components to maximize ethanol production.

SUMMARY OF THE INVENTION

Autolysates of spent yeast have been shown to be an effective nutrient for very high gravity wheat fermentations (Jones and Ingledew, 1994a). Previous studies have described a procedure for the fractionation of yeast into food products (Kollar et al., 1992).

Applicants have found that a soy-hydrolysate based or yeast-autolysate based medium is comparable in cost with a corn steep liquor based medium, but without the problems of availability in particular geographic areas and variations in quality. Soy and other proteins are already widely used as nutrients for many industrial processes (Atkinson et al., 1991; Zabriskie et al., 1988). This patent application shows that crude soy hydrolysates can be used as an effective nutrient supplement for bacterial ethanol fermentations. This media can also be useful for other biotechnology applications. Market values for soybeans and SPEZYME™ FAN protease are approximately $200 metric $ton^{-1}$ and $3 $L^{-1}$, respectively. Using current values for minerals and vitamins, the materials (excluding sugar) for optimized soy fermentation broth, as described herein, are estimated to cost $0.003 $L^{-1}$ ($0.06 $L^{-1}$ of ethanol), equal to that of corn steep liquor-based medium (Asghari et al., 1996), but without the variability in quality, availability problems and toxin problems previously described.

This patent application also shows that a crude yeast autolysate can be used to develop a nutrient medium for ethanol production by *E. coli* KO11.

On site production of autolysate from spent yeasts offers an opportunity for synergy between grain-based and biomass-based ethanol operations. Spent yeasts from grain-based ethanol plants are typically blended with other residues to produce animal feed. Spent yeasts can be "borrowed" for use as a bacterial nutrient. Evaporation of the stillage from bacterial fermentations can recover yeast amino nitrogen together with additional amino nitrogen from bacterial biosynthesis. As described herein, Applicants have discovered a method for the production of ethanol comprising (a) contacting a nutrient medium selected from the group consisting of a pasteurized, hydrolyzed soy product and a pasteurized, autolyzed yeast product, ethanologenic bacteria and a fermentable sugar, thereby obtaining a mixture and (b) incubating said mixture under conditions suitable for the production of ethanol. In the instance that the nutrient medium is a pasteurized, hydrolyzed soy product, it is selected from the group consisting of soy flour, soy meal, ground soybeans and combinations thereof.

The nutrient medium can optionally further comprise a supplement selected from the group consisting of macronutrient salts, vitamins, $FeCl_3$ and combinations thereof. In the instance that a macronutrient salt supplement is optionally included in the nutrient medium, the macronutrient salt supplement can comprise a mixture of $(NH_4)_2SO_4$, $K_2HPO_4$, NaCl and $MgSO_4.7H_2O$. In the instance that a vitamin supplement is optionally included in the nutrient medium, the vitamin supplement can comprise a mixture of cyanocobalamin, calcium pantothenate, pyridoxine.HCl and thiamine.HCl.

In a preferred embodiment, the ethanologenic bacteria of the claimed invention are selected from the group consisting of Erwinia, Klebsiella, Xanthomonas and Escherichia. In a highly preferred embodiment the Escherichia bacteria is *E. coli* KO11.

In another preferred embodiment the conditions suitable for the production of ethanol occurs at a temperature of from about 30° C. to about 40° C. and/or a pH of from about 5.0 to about 7.0.

DETAILED DESCRIPTION OF THE INVENTION

Figure 1:
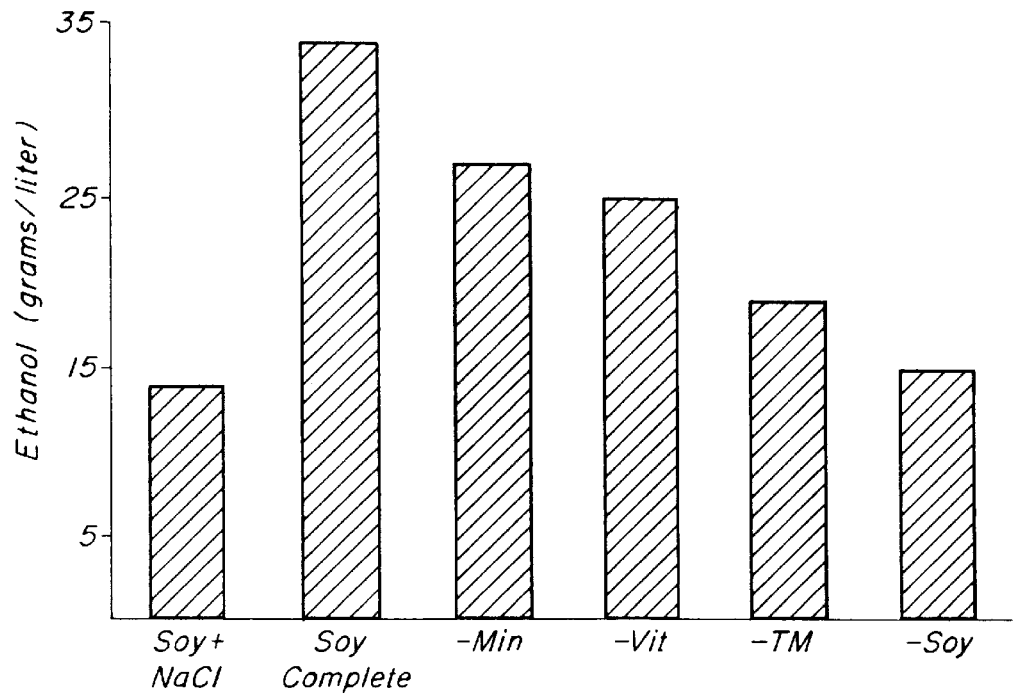
FIG. 1 shows the effect of nutrient supplements on ethanol production in soy hydrolysate-based media after 48 hours of fermentation. Soy+NaCl contained only soy hydrolysate and 5 g NaCl $L^{-1}$. Soy complete contained 50 ml soy flour hydrolysate $L^{-1}$ (Soy), macronutrient salts (Min), vitamins (Vit), and trace metals (TM). Components were omitted as indicated.

Raw soybeans and soybean products, such as soy flour, soy meal, and ground soybeans, are widely available from such sources as grain mills and food processors. Alternatively, a hyrolyzed soybean product can be obtained directly from food processors. A non-hydrolyzed soybean product can be hydrolyzed through the addition of such commercial proteases as SPEZYME™ FAN (Genencor, South San Francisco, Calif.). The conditions for protease hydrolysis are typically selected in consideration of the conditions suitable for the specific protease source. In general, typical conditions include a temperature between about 35° C. and 60° C. and a pH between about 6 and 10. Vitamins, macronutrients, and micronutrients are available through a variety of chemical supply companies, such as Sigma Chemical Company (St. Louis, Mo.). An ethanologenic microorganism is one which has the ability to convert a sugar or oligosaccharide to ethanol. Ethanologenic microorganisms are known in the art and include ethanologenic bacteria. The microorganisms are ethanologenic by virtue of their ability to express one or more enzymes which, individually or together, convert a sugar to ethanol.

Preferred examples of ethanologenic microorganisms include ethanologenic bacteria expressing alcohol dehydrogenase and pyruvate decarboxylase, such as can be obtained with or from *Zymomonas mobilis* (see U.S. Pat. No. 5,028,539 to Ingram et al., U.S. Pat. No. 5,000,000 to Ingram et al., U.S. Pat. No. 5,424,202 to Ingram et al., U.S. Pat. No. 5,487,989 to Fowler et al., U.S. Pat. No. 5,482,846 to Ingram et al., U.S. Pat. No. 5,554,520 to Fowler et al., U.S. Pat. No. 5,514,583 to Picataggio, et al., and copending applications having U.S. Ser. No. 08/363,868 filed on Dec. 27, 1994, U.S. Ser. No. 08/475,925 filed on Jun. 7, 1995, U.S. Ser. No. 08/218,914 filed on Mar. 28, 1994, Attorney Docket No. UF96-01 filed on Apr. 7, 1997, Attorney Docket No. UF97-01 filed on Apr. 7, 1997, Attorney Docket No. UF97-02, filed on Apr. 7, 1997, the teachings of all of which are hereby incorporated by reference, in their entirety).

In another embodiment, the ethanologenic microorganism can express xylose reductase and xylitol dehydrogenase, which convert xylose to xylulose. Xylose isomerase converts xylose to xylulose, as well. The ethanologenic microorganism can further express xylulokinase, which catalyzes the conversion of xylulose to xylulose-5-phosphate. Additional enzymes to complete the pathway can include transaldolase and transketolase. These enzymes can be obtained or derived from *Escherichia coli, Klebsiella oxytoca* and Erwinia species. For example, see U.S. Pat. No. No. 5,514,583.

It is particularly preferred to employ a microorganism which is capable of fermenting both pentoses and hexoses to ethanol, such as are obtained from preparing a recombinant organism which inherently possesses one set of enzymes and which is genetically engineered to contain a complementing set of enzymes. Examples of such microorganisms include those described in U.S. Pat. Nos. 5,000,000; 5,028,539; 5,424,202; 5,482,846; 5,514,583; and Ho et al., WO 95/13362, all of which are incorporated herein by reference. Particularly preferred microorganisms include *Klebsiella oxytoca* P2 and *Escherichia coli* KO11.

Fermentable sugars can be obtained from a wide variety of sources, including lignocellulosic material. Lignocellulose material can be obtained from lignocellulosic waste products, such as plant residues and waste paper. Examples of suitable plant residues include stems, leaves, hulls, husks, cobs and the like, as well as wood, wood chips, wood pulp, and sawdust. Examples of paper waste include discard photocopy paper, computer printer paper, notebook paper, notepad paper, typewriter paper, and the like, as well as newspapers, magazines, cardboard, and paper-based packaging materials.

A cellulase enzyme can be added to the lignocellulosic material. The cellulase can be provided as a purified enzyme or can be provided by a cellulase-producing microorganism in said aqueous mixture. Cellulases, as that term is used herein, includes any enzyme that effects the hydrolysis or otherwise solubilizes cellulase (including insoluble cellulose and soluble products of cellulose). Cellulase enzymes, including purified enzyme preparations, organisms expressing the same, are known in the art. Suitable sources of cellulase include such commercial cellulase products as SPEZYME™ CP, CYTOLASE™ M104, and MULTI-FECT™ CL (Genencor, South San Francisco, Calif.), and such organisms expressing cellulase as the recombinant bacterium of U.S. Pat. No. 5,424,202, which is incorporated herein by reference.

The conditions for cellulase hydrolysis are typically selected in consideration of the conditions suitable for the specific cellulase source, e.g, bacterial or fungal. For example, cellulase from fungal sources typically works best at temperatures between about 30° C. and 48° C. and a pH between about 4.0 and 6.0. In general, typical conditions include a temperature between about 30° C. and 60° C. and a pH between about 4.0 and 8.0.

The conditions for converting sugars to ethanol are typically those described in the above referenced U.S. patents. Generally, the temperature is between about 30° C. and 40° C. and the pH is between about 5.0 and 7.0.

It is generally advantageous to add supplements to the nutrient medium, such as vitamins, macronutrients, and micronutrients. Vitamins include choline chloride, nicotinic acid, thiamine HCl, cyanocobalamin, p-aminobenzoic acid, biotin, calcium pantothenate, folic acid, pyridoxine.HCl, and riboflavin. Macronutrients include $(NH_4)_2SO_4$, $K_2HPO_4$, NaCl, and $MgSO_4.7H_2O$. Micronutrients include $FeCl_3.6H_2O$, $ZnCl_2.4H_2O$, $CoCl_2.6H_2O$, molybdic acid (tech), $CUCl_3.2H_2O$, $CaCl_2.2H_2O$, and $H_3BO_3$.

Methods and Materials

The methods and materials described below were used in carrying out the work described in the examples which follow. Materials and methods for a soy hydrolysate-based nutrient medium are described first, followed by a yeast autolysate-based nutrient medium.

Soy Hydrolysate-based Nutrient Medium

TRYPTONE™, SOYTONE™ and yeast extract were obtained from Difco (Detroit, Mich., USA). Soybeans, soy flour, and soy meal were purchased locally (approximately 8% moisture). The particular size of soybeans and soy meal was reduced with a commercial coffee grinder prior to digestion. SPEZYME™ FAN protease was generously provided by Genencor International (South San Francisco, Calif., USA).

Soy hydrolysates prepared by different methods were tested in shaken, 250-ml flasks (50 ml broth, 35° C.). Media for flask-fermentations (and for initial studies in pH-stats) contained per liter: 50 ml of test hydrolysate, 100 g glucose, 2 g $(NH_4)_2SO_4$, 1 g $K_2HPO_4$, 2 g NaCl, 0.25 g $MgSO_4.7H_2O$, 5.4 mg $FeCl_3.6H_2O$, 0.4 mg $ZnCl_2.4H_2O$, 0.4 mg $CoCl_2.6H_2O$, 0.4 mg molybdic acid (tech), 0.2 mg $CUCl_3.2H_2O$, 0.2 mg $CaCl_2.2H_2O$, 0.1 mg $H_3BO_3$, 2 mg choline chloride, 2 mg nicotinic acid, 1 mg thiamine.HCl, 0.1 $\mu$g cyanocobalamin, 0.2 $\mu$g p-aminobenzoic acid, 0.2 $\mu$g biotin, 0.4 $\mu$g calcium pantothenate, 0.2 $\mu$g folic acid, 0.2 $\mu$g pyridoxine.HCl, and 0.2 $\mu$g riboflavin. Flasks were inoculated by transferring a small colony from solid media. Ethanol produced after 24 h was used as the endpoint. Ethanol was determined by gas chromatography (Beall et al., 1991). Free amino nitrogen was determined spectrophotometrically using glycine as a standard (European Brewery Convention et al., 1987).

Combinations of mineral and vitamin-supplements were tested in pH-stats (350 ml working volume, pH 6.0, 35° C., 100 rpm) (Beall et al., 1991). These were inoculated from broth cultures to an initial density of 165 mg cell dry weight $L^{-1}$. Optimized soy-based medium contained per liter: 50 ml crude soy hydrolysate (9.2 g soy solids $L^{-1}$) or 5 g TRYPTONE™, 100 g glucose, 2 g $(NH_4)_2SO_4$, 1 g $K_2HPO_4$, 2 g NaCl, 0.25 g $MgSO_4.7H_2O$, 10.8 mg $FeCl_3.6H_2O$, 0.25 mg thiamine.HCl, 0.1 $\mu$g calcium pantothenate, 0.05 $\mu$g pyridoxine.HCl, and 0.02 $\mu$g cyanocobalamin.

Ethanol production by *E. coli* KO11 (flask cultures) was used as a bioassay to optimize the denaturation and hydrolysis of soy with SPEZYME™ FAN. The resulting procedure for the production of a 20-fold nutrient concentrate (300 ml) was: 1) combine 60 g soy flour, ground soybeans or soy meal (approximately 8% moisture) with 220 ml tap water in a 500-ml screw-capped Erlenmeyer flask (approximately pH 8); 2) denature by heating to 95° C. for 2 h with reciprocal shaking; 3) cool to room temperature and adjust to pH 9 with 10 N sodium hydroxide; 4) add 20 ml of 95% ethanol and 1.2 ml of SPEZYME™ FAN; 5) mix thoroughly and incubate for 18 h at 50° C. with reciprocal shaking. Hydrolysates were stored frozen until needed and pasteurized for 15 min at 90° C. immediately before use. Inclusion of ethanol in the hydrolysate appeared to increase the efficacy of pasteurization. Approximately 50% of soy dry weight was solubilized with a free amino nitrogen content of 1.0 g $L^{-1}$.

Yeast-based Nutrient Medium

*E. coli* KO11 was used in these studies. Unless noted otherwise, media for pH-stats contained per liter: macronutrient mineral salts (2 g $(NH_4)_2SO_4$, 1 g $K_2HPO_4$, and 2 g NaCl); 0.5 g $MgSO(_4).7H_2O$, 11 mg $FeCL_3.6H_2O$; vitamins (25 $\mu$g cyanocobalamin, 100 $\mu$g calcium pantothenate, 50 $\mu$g pyridoxine.HCl, and 500 $\mu$g thiamine.HCl), complex nutrient (5 g Difco product of 10 g crude yeast autolysate), 100 g glucose, and 40 mg chloramphenicol. A chloramphenicol stock (1000×) was prepared in 70% ethanol. Inocula for pH-stats were grown for 18 h at 30° C. in LBG medium (Luria and Delbruck, 1943) (per liter: 50 g glucose, 5 g Difco Yeast Extract, 10 g Difco Tryptone, 5 g sodium chloride) and 40 mg chloramphenicol. Cells were harvested by centrifugation (5,000× g, 5 min) for use as inocula (158 mg dry weight $L^{-1}$)

Pressed yeast cakes were purchased from a local bakery. Inorganic salts, except molybdic acid (technical), were reagent grade. Salts, Difco Tryptone, Difco Soytone and Difco Yeast Extract were purchased from the Fisher Scientific Company (Norcross, Ga.). Chloramphenicol was purchased from the Sigma Chemical Company (St. Louis, Mo.).

A crude yeast autolysate was prepared in batches by a modification of the method described by Kollar et al., (1992). Sufficient water was added to 200 g of yeast cake (70% moisture; 200 g dry weight $L^{-1}$), 3 g NaCl, and 16 g ethanol (20 ml) to produce a total volume of 300 ml. A glass marble was added to aid agitation (60 cycles $min^{-1}$) and the mixture incubated in a sealed 500-ml flask for 24 h at 50° C. This serves as a 20-fold concentrate and was stored frozen at −20° C. Autolysate was pasteurized (15 min, 90° C.) immediately prior to use (final concentration of 10 g autolyzed yeast $L^{-1}$).

Modified Corning FLEAKERS™ (500 ml total volume, 350 ml working volume) were used as vessels for pH-stats (Beall et al., 1991). These were immersed in a 35° C. water bath and agitated with a magnetic stir bar (100 rpm). Broth pH was controlled during fermentation by the automatic addition of 2N KOH and was not allowed to fall below pH 6.0. Ethanol, base consumption and pH were measured at 24 h intervals.

Ethanol was measured by gas liquid chromatography using isopropanol as an internal standard (Ohta et al., 1991). Ethanol yields were calculated after correcting for dilution by added base and for ethanol present at the time of inoculation (yeast autolysate and chloramphenicol stock). Yields are expressed as a percentage of the maximum theoretical yield (51 g ethanol per 100 g glucose) and were not corrected for unmetabolized sugar. Moisture content was measured after drying for 48 h at 70° C. Free amino nitrogen (FAN) was measured using glycine as a standard (European Brewery Convention, 1987).

Kollar et al., (1992) developed an optimal batch procedure for yeast autolysis (100 g autolyzed yeast $L^{-1}$) based on the solubilization of protein. This procedure included freshly prepared autolysate (prior batch), 1% NaCl and 5% (w/v) ethanol. Initial experiments, using ethanol production by *E. coli* KO11 (48 h) as a bioassay, indicated that the yeast concentration can be doubled to produce a nutrient which was equivalent on a dry weight basis. Using this higher yeast concentration eliminated any benefit from the addition of autolysate from a prior batch. Approximately 58% of the yeast dry weight was solubilized during the preparation of 20% yeast autolysate.

EXAMPLE 1

Soy Hydrolysate-based Medium

Using the materials and procedures outlined above, vitamin and mineral supplements were optimized for soy hydrolysate-based medium (9.2 g $L^{-1}$ total soy, 4.6 g $L^{-1}$ soy solubles), using ethanol production by *E. coli* KO11 as a measure. FIG. 1 shows the beneficial effects of supplements on ethanol production. Subsequent experiments indicated that $FeCl_3$ can fully replace the mixture of trace metals. Only 4 of the 10 vitamins tested were beneficial: thiamine.HCl, cyanocobalamin, calcium pantothenate and pyridoxine.HCl. When compared on the basis of solubles, soy hydrolysate prepared as described was equivalent to commercial SOY- TONE™ as a nutrient for ethanol production (44–45 g ethanol L$^{-1}$). Neither fermentation rate nor ethanol yield was increased significantly by increasing the levels of vitamins or minerals above that in the optimized soy medium.

Figure 2:
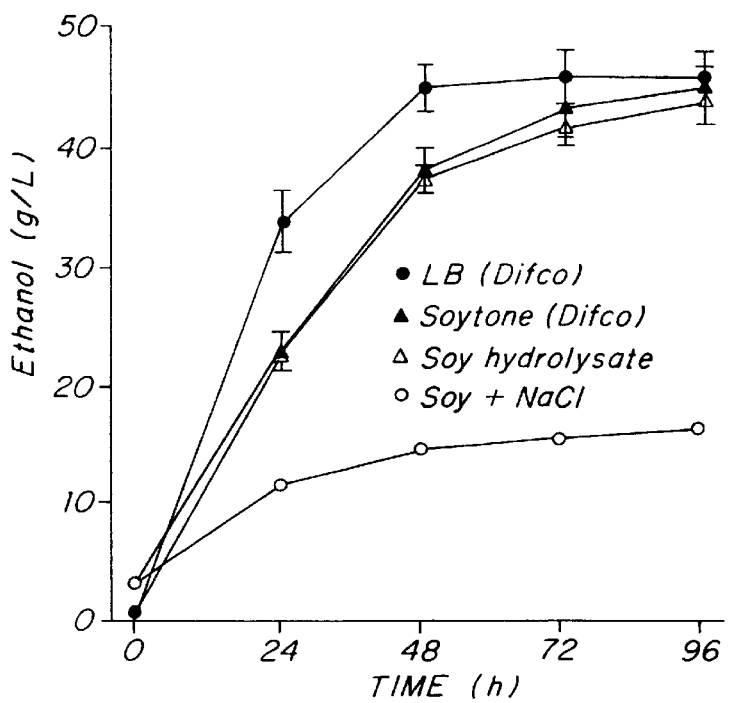
FIG. 2 shows a comparison of optimal soy hydrolysate-based medium to LB and Soytone (5 g $L^{-1}$)-based medium. Standard deviations (n≧6) are indicated by error bars for LB, Soytone, and Soy hydrolysate media.

Fermentations were also conducted in modified LB medium (Luria and Delbruck, 1943) (per liter: 10 g TRYPTONE™, 5 g Yeast Extract, 5 g NaCl, and 100 g glucose) for comparison. No combination of vitamins and minerals was found which allowed fermentations with soy hydrolysate (4.6 g soy solubles L$^{-1}$) to reach completion as rapidly as fermentations with LB medium (15 g soluble hydrolysate L$_{-1}$) The completion of fermentations in soy medium can be slower due to the increased demand for amino acid biosynthesis. Final ethanol concentrations achieved with both media were nearly equivalent (FIG. 2).

EXAMPLE 2
Yeast Autolysate-based Medium

Figure 3:
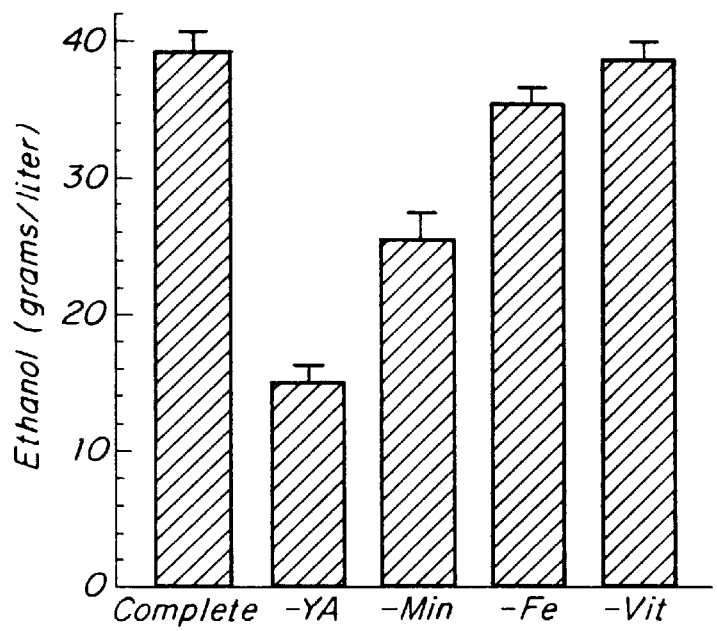
FIG. 3 shows the effect of nutrient supplements on ethanol production in yeast autolysate-based media after 48 hours of fermentation (10% glucose). Complete medium contained 50 ml yeast autolysate $L^{-1}$ (YA), macronutrient salts (Min), vitamins (Vit), and $FeCl_3.6H_2O$ (Fe). Components were omitted as indicated.

A series of experiments was conducted with 20%-yeast autolysate to determine how to optimize the supplements (macronutrient salts, magnesium, trace metals, and vitamins) for ethanol production. An initial mixture of 7 trace metals was completely replaced by FeCl$_3$ (11 mg L$^{-1}$) Similarly, a mixture of 10 vitamins was reduced to 4 vitamins (per liter: 25 μg cyanocobalamin, 100 μg calcium pantothenate, 50 μg pyridoxine.HCl, and 500 μg thiamine.HCl). FIG. 3 and Table 1 illustrate the effect of omitting either of these supplements.

Figure 4:
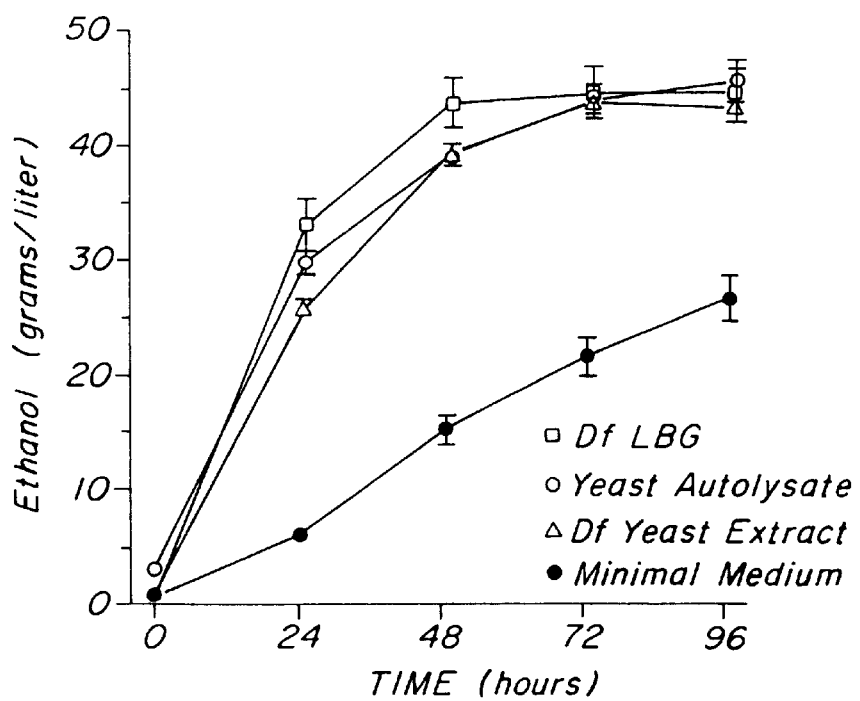
FIG. 4 shows a comparison of complete yeast autolysate-based medium to Difco nutrient-based medium. Results with minimal medium plus vitamins (no complex supplements) are also included.

Inorganic sources of nitrogen (2 g (NH$_4$)$_2$SO$_4$ L$^{-1}$) and phosphorous (1 g K$_2$HPO$_4$ L$^{-1}$) were also beneficial (FIG. 3; Table 1). A further increase in ethanol production was obtained with a 50% increase in the level of ammonia, phosphate, or both. Reducing either macronutrient or magnesium resulted in lower ethanol concentrations and lower yields. As a complex nutrient, 20%-yeast autolysate was clearly superior to 10%-yeast autolysate (Table 1). The more concentrated nutrient also has the advantage of reducing the volumes which must be processed. Omission of yeast autolysate reduced fermentation rates by over 50% (FIGS. 3 & 4). Reductions in the level of yeast autolysate (25% and 50%) also reduced the rates of ethanol production and ethanol yields.

The addition of SPEZYME™ protease (4 ml L$^{-1}$) during autolysis did not appear to improve the nutritional value of autolysate when assayed at a 1:20 dilution (Table 1). When tested at one-half strength, however, autolysate containing protease supported higher rates of ethanol production and a higher product yield than control autolysate. The addition of 50% higher levels of ammonia and phosphate also improved fermentations with half-strength hydrolysate but yields remained below that obtained with full strength autolysate.

Ethanol yield with crude yeast autolysate and optimal supplements was equivalent to that obtained with LBG (FIG. 4; Table 1) albeit with a slightly slower rate of ethanol production. The nutritional value of crude yeast autolysate was compared to Difco products (Table 1). When compared using the same supplements, 20%-yeast autolysate diluted to 10 g autolyzed yeast L$^{-1}$ was equivalent to 5 gL$^{-1}$ Yeast Extract or Soytone but less effective than Tryptone. The FAN contents of these fermentation media were examined as a possible bias for the nutritional differences (Jones and Ingledew, 1994b; Thomas and Ingledew, 1990). LBG (475 mg L$^{-1}$) contained the highest level of FAN, followed by protease-supplemented yeast autolysate (225 mg L$^{-1}$), Yeast Extract (177 mg L$^{-1}$), yeast autolysate (168 mg L$^{-1}$), Tryptone (149 mg L$^{-1}$) and Soytone (83 mg L$^{-1}$). Although it is clear that complex nutrients containing amino acids stimulate fermentation, factors other than FAN content must also contribute to the effectiveness.

TABLE 1

Effects of nutrients on fermentation (100 g glucose/l)

| Nutrients[a,b,c] | n[d] | Ethanol (g/l) | Base[e] (ml/l) | Yield (% theoretical) |
|---|---|---|---|---|
| 1. LBG medium (Difco) | 23 | 44.7 ± 1.9 | 62.9 | 92 |
| Difco nutrient (g/l) + salts + Mg + Fe + vitamins | | | | |
| 2. Yeast Extract (5) | 4 | 43.7 ± 0.9 | 62.9 | 90 |
| 3. Tryptone (5) | 3 | 47.9 ± 0.5 | 51.4 | 97 |
| 4. Soytone (5) | 6 | 44.8 ± 1.7 | 54.3 | 91 |
| 10%-Yeast Autolysate Ca yeast/l) + salts + Mg + Fe + vitamins | | | | |
| 5. yeast autolysate (10) | 3 | 44.3 ± 0.5 | 77.1 | 83 |
| 20-Yeast Autolysate (g yeast/l) + salts + Mg + FE + vitamins | | | | |
| 6. yeast autolysate (10) | 21 | 46.0 ± 1.7 | 68.6 | 90 |
| 7. #6 minus Fe | 3 | 44.7 ± 1.2 | 62.9 | 87 |
| 8. #6 minus salts | 3 | 29.7 ± 5.4 | 97.1 | 58 |
| 9. #6 minus vitamins | 6 | 41.3 ± 3.2 | 91.4 | 83 |
| 10. #6 minus yeast autolysate | 4 | 26.7 ± 1.9 | 71.4 | 50 |
| 11. #6 plus protease | 3 | 44.2 ± 1.5 | 85.7 | 88 |
| 12. #6 with 1.5× Mg | 2 | 43.5 | 71.4 | 86 |
| 13. #6 with 1.5× NH$_4$ | 2 | 47.6 | 54.3 | 93 |
| 14. #6 with 1.5× PO$_4$ | 2 | 48.7 | 57.1 | 95 |
| 15. #6 with 1.5× [NH$_4$ + PO$_4$] | 4 | 47.0 ± .1 | 62.9 | 92 |
| 16. #6 with 0.5× Mg | 2 | 42.5 | 94.3 | 85 |
| 17. #6 with 0.5× NH$_4$ | 2 | 42.7 | 114.3 | 87 |
| 18. #6 with 0.5× PO$_4$ | 2 | 44.5 | 80.0 | 88 |
| 19. #6 with 0.75× yeast autolysate | 4 | 42.9 ± 4.6 | 62.9 | 85 |
| 20. #6 with 0.5× yeast autolysate | 5 | 35.8 ± 2.3 | 77.1 | 72 |
| 21. #20 with protease[d] | 3 | 39.9 ± 0.5 | 94.3 | 82 |
| 22. #20 with 1.5× NH$_4$ | 2 | 41.4 | 65.7 | 83 |
| 23. #20 with 5.× [NH$_4$ + PO$_4$] | 2 | 38.9 | 62.9 | 77 |

[a]Abbreviations: Mg, MgSO$_4$.7H$_2$O; Fe, FeCl$_3$.6H$_2$O; NH$_4$; and PO$_4$, K$_2$HPO$_4$.
[b]Average initial ethanol concentrations in fermentation broth were as follows: 0.7 g/l for LBG and Difco products; 5.3 g/l for 10%-Yeast Autolysate; 3.0 g/l for 20%-Yeast Autolysate (2.4 g/l for 0.75× and 1.9 g/l for 0.5×).
[c]Omitted salts were replaced by an equivalent weight of NaCl.
[d]Number of fermentation trials.
[e]2N NaOH added to maintain pH during fermentation.
[f]Yeast autolysate prepared with SPEZYME ™ FAN protease (4 m/l) as a supplement.

EQUIVALENTS

Those skilled in the art will recognize, or be able to ascertain using no more than routine experimentation, many equivalents to the specific embodiments of the invention described herein. Such equivalents are intended to be encompassed by the following claims.

REFERENCES

Amartey, S. and T. W. Jeffries, "Comparison of corn steep liquor with other nutrients in the fermentation of D-xylose by Pichia stipitis CBS 6054" *Biotechnol. Lett.,* 16:211–214 (1994).

Asghari, A., R. J. Bothast, J. B. Doran, L. O. Ingram, "Ethanol production from hemicellulose hydrolysates of agricultural residues using genetically engineered *Escherichia coli* strain KO11" *J Ind. Microbiol.,* 16:42–47 (1996).

Atkinson, B. and F. Mavituna, *Biochemical Engineering and Biotechnology Handbook,* 2nd edn. Stockton Press, New York, N.Y. (1991).

Beall, D. S., L. O. Ingram, A. Ben-Bassat, J. B. Doran, D. E. Fowler, R. G. Hall and B. E. Wood "Conversion of hydrolysates of corn cobs and hulls into ethanol by recombinant *Escherichia coli* B containing integrated genes for ethanol production", *Biotechnol. Lett.*, 14:857–862 (1992).

Beall, D. S., K. Ohta and L. O. Ingram, "Parametric studies of ethanol production from xylose and other sugars by recombinant *Escherichia coli*" *Biotechnol Bioeng.*, 38:296–303 (1991).

Brooks, T. A. and L. O. Ingram, "Conversion of mixed office paper to ethanol by genetically engineered *Klebsiella oxytoca* strain P2" *Biotechnol. Progr.*, 11:619–625 (1995).

European Brewery Convention, 1987. "Free amino nitrogen" In *Analytica-EBC*, 4th edn., pp E141–E142, European Brewery Convention, Zurich, Switzerland.

Guimaraes, W. V., G. L. Dudey and L. O. Ingram, "Fermentation of sweet whey by ethanologenic *Escherichia coli*" *Biotechnol Bioeng.*, 40:41–45 (1992).

Hohmann, N. and C. M. Rendleman, "Emerging technologies in ethanol production" US Department of Agriculture Information Bulletin Number 663, pp. 1–17 (1993).

Jones, A. M. and W. M. Ingledew, "Fermentation of very high gravity wheat mash prepared using fresh yeast autolysate" *Biores. Technol.*, 50:97–101 (1994a).

Jones, A. M. and W. M. Ingledew, "Fuel alcohol production: appraisal of nitrogenous yeast foods for very high gravity wheat mash fermentation" *Process Biochem.*, 29:483–488 (1994b).

Lawford, H. G. and J. D. Rousseau, "Ethanol production by recombinant *Escherichia coli* carrying genes from *Zymomonas mobilis*" *Appl Biochem Biotechnol.*, 28/29:221–236 (1991).

Katzen, R. and D. E. Fowler, *Appl. Biochem. Biotechnol.*, 45/46:697–707 (1994).

Kollar, R., E. Sturdik and J. Sajbidor, "Complete fractionation of *Saccharomyces cerevisiae* biomass", *Food Biotechnol.*, 6:225–237 (1992).

Luria, S. E. and M. Delbruck, "Mutations of bacteria from virus sensitivity to virus resistances" *Genetics* 28:491–511 (1943).

Ohta, K., D. S. Beall, J. P. Mejia, K. T. Shanmugam and L. O. Ingram, "Genetic improvement of *Escherichia coli* for ethanol production: chromosomal integration of *Zymomonas mobilis* encoding pyruvate decarboxylase and alcohol dehydrogenase II" *Appl Environ Microbiol.*, 57:893–900 (1991).

Shah, M. M. and M. Cheryan, "Acetate production by *Clostridium thermoaceticum* in corn steep liquor media", J. Indust. Microbiol., 15:424–428 (1995).

Sheehan, J. J., "Bioconversion for production of renewable transportation fuels in the United States: a strategic perspective" *In Enzymatic Conversion of Biomass for Fuels Production*, ACS Symposium Series 566 (Himmel M. E., J. O. Baker and R. P. Overend, eds.), pp 1–53, American Chemical Society, Washington, D.C. (1994).

Thomas, K. C. and W. M. Ingledew, "Fuel alcohol production: effects of free amino nitrogen on fermentation of very-high-gravity wheat-mashes" *Appl. Environ Microbiol.*, 56:2046–2050 (1990).

Zabriskie D. W., W. B. Armiger, D. H. Phillips and P. A. Albano, *Traders' Guide to Fermentation Media Formulation*, Traders Protein, Memphis, Tenn. (1988).

What is claimed is:

1. A method for the production of ethanol comprising
    (a) contacting a nutrient medium selected from the group consisting of a pasteurized, hydrolyzed soy product and a pasteurized, autolyzed yeast product, with an ethanologenic bacteria and a fermentable sugar, thereby obtaining a mixture and
    (b) incubating said mixture under conditions suitable for the production of ethanol at a temperature of from about 30° C. to about 40° C. such that ethanol is produced.

2. The method of claim 1, wherein said nutrient medium is a pasteurized, hydrolyzed soy product selected from the group consisting of soy flour, soy meal, ground soybeans and combinations thereof.

3. The method of claim 1, wherein step (a) further comprises a supplement selected from the group consisting of macronutrient salts, vitamins, $FeCl_3$ and combinations thereof.

4. The method of claim 3, wherein said supplement comprises a macronutrient salt mixture comprising $(NH_4)_2SO_4$, $K_2HPO_4$, NaCl and $MgSO_4.7H_2O$.

5. The method of claim 3, wherein said supplement comprises a vitamin mixture comprising cyanocobalamin, calciumpantothenate, pyridoxine.HCl and thiamine.HCl.

6. The method of claim 1, wherein said ethanologenic bacteria are selected from the group consisting of Erwina, Klebsiella, Xanthomonas and Escherichia.

7. The method of claim 6, wherein said Escherichia bacteria is *E. coli* KO11.

8. The method of claim 1, wherein said conditions suitable for the production of ethanol occurs at a pH of from about 5.0 to about 7.0.

9. A method for the production of ethanol comprising
    (a) contacting a nutrient medium selected from the group consisting of a pasteurized, hydrolyzed soy product and a pasteurized, autolyzed yeast product, with an ethanologenic bacteria and a fermentable sugar, thereby obtaining a mixture and
    (b) incubating said mixture under conditions suitable for the production of ethanol at a pH of from about 5.0 to about 7.0 such that ethanol is produced.

10. The method of claim 9, wherein said nutrient medium is a pasteurized, hydrolyzed soy product selected from the group consisting of soy flour, soy meal, ground soybeans and combinations thereof.

11. The method of claim 9, wherein step (a) further comprises a supplement selected from the group consisting of macronutrient salts, vitamins, $FeCl_3$ and combinations thereof.

12. The method of claim 11, wherein said supplement comprises a macronutrient salt mixture comprising $(NH_4)_2SO_4$, $K_2HPO_4$, NaCl and $MgSO_4.7H_2O$.

13. The method of claim 11, wherein said supplement comprises a vitamin mixture comprising cyanocobalamin, calciumpantothenate, pyridoxine.HCl and thiamine.HCl.

14. The method of claim 9, wherein said ethanologenic bacteria are selected from the group consisting of Erwinia, Klebsiella, Xanthomonas and Escherichia.

15. The method of claim 14, wherein said Escherichia bacteria is *E coli* KO11.

* * * * *

UNITED STATES PATENT AND TRADEMARK OFFICE
CERTIFICATE OF CORRECTION

| | |
|---|---|
| PATENT NO. | : 6,130,076 |
| APPLICATION NO. | : 08/879005 |
| DATED | : October 10, 2000 |
| INVENTOR(S) | : Lonnie O. Ingram |

Page 1 of 1

It is certified that error appears in the above-identified patent and that said Letters Patent is hereby corrected as shown below:

Title page, item [75] inventors: add -- Seam W. York --.

Signed and Sealed this

Twenty-fifth Day of September, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,130,076 | Page 1 of 1 |
| APPLICATION NO. | : 08/879005 | |
| DATED | : October 10, 2000 | |
| INVENTOR(S) | : Lonnie O. Ingram et al. | |

It is certified that error appears in the above-identified patent and that said Letters Patent is hereby corrected as shown below:

Title Page, Item (75) Inventors should read

-- Lonnie O. Ingram, Gainesville, FL (US);
  Sean W. York, Gainesville, FL (US) --.

In the Specification:

Column 1, Line 10, after the period following the parenthetical "(Publication Nos. R-05029 and R-05050)" add the following sentence:

-- The Government has certain rights in the invention. --.

This certificate supersedes the Certificate of Correction issued September 25, 2007.

Signed and Sealed this
Thirty-first Day of May, 2011

David J. Kappos
*Director of the United States Patent and Trademark Office*